United States Patent
Pollonini et al.

(10) Patent No.: US 10,722,129 B2
(45) Date of Patent: Jul. 28, 2020

(54) IMAGING SYSTEM FOR INTRA-OPERATIVE AND POST-OPERATIVE BLOOD PERFUSION MONITORING

(71) Applicants: UNIVERSITY OF HOUSTON SYSTEM, Houston, TX (US); THE METHODIST HOSPITAL, Houston, TX (US)

(72) Inventors: Luca Pollonini, Manvel, TX (US); Scott E. Parazynski, Houston, TX (US); Kiefer Forseth, Houston, TX (US)

(73) Assignees: University of Houston System, Houston, TX (US); The Methodist Hospital, Houston, TX (US)

(*) Notice: Subject to any disclaimer, the term of this patent is extended or adjusted under 35 U.S.C. 154(b) by 56 days.

(21) Appl. No.: 16/104,750

(22) Filed: Aug. 17, 2018

(65) Prior Publication Data

US 2019/0000328 A1 Jan. 3, 2019

Related U.S. Application Data

(62) Division of application No. 14/537,509, filed on Nov. 10, 2014, now Pat. No. 10,080,504.

(60) Provisional application No. 61/902,054, filed on Nov. 8, 2013.

(51) Int. Cl.
*A61B 5/1455* (2006.01)
*A61B 5/026* (2006.01)
*A61B 5/00* (2006.01)

(52) U.S. Cl.
CPC ........ *A61B 5/0261* (2013.01); *A61B 5/14551* (2013.01); *A61B 5/441* (2013.01); *A61B 5/742* (2013.01)

(58) Field of Classification Search
CPC . A61B 5/0059; A61B 5/1455; A61B 5/14551; A61B 5/6814; A61B 5/72; A61B 5/7271; A61B 5/14553
See application file for complete search history.

(56) References Cited

U.S. PATENT DOCUMENTS

| 6,264,610 B1 | 7/2001 | Zhu |
| 7,239,903 B2 | 7/2007 | Hideo |
| 8,929,967 B2 * | 1/2015 | Mao .................. A61B 5/14532 600/344 |
| 2001/0035503 A1 | 11/2001 | Quistorff et al. |
| 2003/0139667 A1 | 7/2003 | Hewko et al. |
| 2008/0177163 A1 | 7/2008 | Wang et al. |
| 2010/0042004 A1 | 2/2010 | Dhawan |

(Continued)

OTHER PUBLICATIONS

International Search Report and Written Opinion issued in PCT/US2014/064844 dated May 5, 2015.

(Continued)

*Primary Examiner* — Eric F Winakur
(74) *Attorney, Agent, or Firm* — Parker Highlander PLLC

(57) ABSTRACT

Embodiments described herein generally relate to devices, methods and systems for determining blood oxygenation. By applying near infrared radiation of an appropriate wavelength to the tissue and determining the absorbance at a plurality of points where the distance between the source of the near infrared radiation and the detector are known, the oxygenation state of the hemoglobin can be determined based on position in a three dimensional space.

8 Claims, 11 Drawing Sheets

(56) References Cited

U.S. PATENT DOCUMENTS

| | | | |
|---|---|---|---|
| 2011/0205535 A1* | 8/2011 | Soller | A61B 5/14552 356/300 |
| 2013/0012794 A1 | 1/2013 | Zeng et al. | |
| 2013/0023744 A1* | 1/2013 | Benni | A61B 5/746 600/339 |
| 2013/0090541 A1 | 4/2013 | MacFarlane et al. | |

OTHER PUBLICATIONS

Restriction Requirement Action issued in U.S. Appl. No. 14/537,509 dated Jan. 13, 2017.
Official Action issued in U.S. Appl. No. 14/537,509 dated Jul. 3, 2017.

* cited by examiner

IMAGING SYSTEM FOR INTRA-OPERATIVE AND POST-OPERATIVE BLOOD PERFUSION MONITORING

CROSS-REFERENCE TO RELATED APPLICATIONS

This application is a divisional application of U.S. patent application Ser. No. 14/537,509 filed Nov. 10, 2014, which is a non-provisional application of U.S. provisional patent application Ser. No. 61/902,054, filed Nov. 8, 2013, which is herein incorporated by reference.

BACKGROUND

Field

Embodiments disclosed herein generally relate to devices, methods and systems for measuring tissue perfusion.

Description of the Related Art

Reconstructive surgeries, such as flap surgery, consist of the transplantation of healthy tissue, such as a skin graft or flap, from a donor site to a wounded recipient area affected by loss of tissue. The loss of tissue may be related to a specific trauma, such as trauma due to burn, laceration or cancer removal. The transplanted tissue usually comprises skin, underlying adipose tissue, or muscle, but it can also consist of composite tissues (skin and fat, skin and fat and muscle, etc.) or other organs. When possible, the tissue is transplanted from a nearby area without disconnecting the vascular network. However, in certain cases, the tissue must be transplanted from a different area of the body (also referred to as a free flap), and the vascular network is reconnected to the existing blood vessels of the recipient area.

After detachment from the donor site, whether transplanted from a nearby area or different area of the body, it is crucial to re-establish blood perfusion throughout the transplanted tissue in a timely manner and with high accuracy to guarantee a successful long-term outcome. If the tissue is not properly perfused in a timely fashion, the tissue will die through a process known as necrosis. A number of techniques have been developed to determine whether the tissue has been properly perfused, with varying levels of success.

During the reconstructive procedure, surgeons can use a Doppler ultrasound pencil probe to assess if blood flow is re-established in the vessels underneath the transplanted skin. Although of some value, this method only allows coarse assessment of blood flow in major vessels by producing audible feedback which is indicative of blood flow to the surgeon. Specifically, ultrasound techniques can grossly show that blood flow is being received by the area, but they do not provide information regarding the direction of blood flow or the oxygenation of the blood received by the transplanted tissue. Doppler ultrasound is sensitive to blood flow, primarily in arteries and arterioles. Doppler ultrasound relies on the technique and the interpretation of the surgeon of the whooshing sound produced by the Doppler device in response to detected blood flow, which is highly subjective and sensitive to technique. Oftentimes this leads to a binary interpretation ("flow/no flow") that does not represent the accurate status of tissue oxygenation, and might lead to inaccurate clinical decisions. Moreover, the technique gives no measure of perfusion at the periphery of the transplanted tissue, as it is supplied by much smaller capillaries which are not detectable by use of the Doppler device.

Contrast medium imaging using fluorescent dye is an effective methodology to infer information about circulation in large and medium-sized vessels, but it does not provide reliable information on microcirculation in the transplanted tissue. In addition, it is inherently qualitative and its applicability is limited to the operating room where internal tissues are exposed to direct illumination of the imaging system.

Laser Doppler Flowmetry (LDF) is another technique which has been used to determine blood perfusion. In LDF, a beam of laser light is delivered to a volume of tissue. Blood cells in the volume of tissue which are struck by laser light will partly reflect it, whereupon the light undergoes a Doppler shift. The light in the volume of tissue will be a mixture of unshifted and Doppler-shifted components, the magnitude and frequency distribution of the latter being related to the number and velocity of moving blood cells within the volume of tissue. Similar to contrast medium imaging, LDF can provide imaging of blood perfusion only in superficial skin layers, i.e., tenths of microns below the skin surface.

Near Infrared Spectroscopy (NIRS) has been shown to be useful in plastic surgery and transcranial oxygenation detection. NIRS uses near infrared (NIR) radiation to penetrate the underlying tissue where specific frequencies will be absorbed or back-scattered primarily based on the oxygenation state of hemoglobin. However, current NIRS devices and methods determine oxygenation at a single point or region without mapping or providing oxygenation data based on depth at multiple points in real time.

Thus, there is a need in the art for better visualization of the blood flow and the oxygenation state of the blood, and to track changes over time (including after a patient has been discharged home following surgery).

SUMMARY

The embodiments described herein generally relate to methods, devices and systems for visualization of blood flow and oxygenation.

In one embodiment, an imaging device can include a support comprising a first surface; a plurality of first radiation sources positioned at a first interval on the first surface, each of the plurality of first radiation sources delivering radiation at a first interval and a first wavelength range, the first wavelength range comprising one or more first wavelengths between about 650 nm and about 1000 nm; a plurality of second radiation sources positioned at the first surface, the second radiation sources delivering radiation at a second interval and a second wavelength range, the second wavelength range comprising one or more second wavelengths between about 650 nm and about 1000 nm, at least one of the one or more second wavelengths being different than at least one of the one or more first wavelengths, wherein each of the plurality of second radiation sources is positioned adjacent one of the plurality of first radiation sources creating a plurality of associated radiation sources; and a detector positioned at the first surface, the detector positioned a first distance from each of the first radiation sources and each of the second radiation sources, and the detector detecting radiation at wavelengths between 650 nm and 1000 nm.

In another embodiment, a method for tissue imaging transplanted tissue can include positioning a first radiation source and a second radiation source in proximity to a tissue;

delivering a first radiation of a first wavelength range from the first radiation source to the tissue, the first wavelength range being between about 650 nm and about 1000 nm, the tissue absorbing a portion of the first radiation creating a first transmitted radiation; detecting the first transmitted radiation at a detector positioned a first distance from the first radiation source, wherein the path traveled by the first transmitted radiation through the tissue creates a first mean radiation path; delivering a second radiation of a second wavelength range from the second radiation source to the tissue, the second wavelength range being between about 650 nm and about 1000 nm, wherein the tissue absorbs a portion of the second radiation creating a second transmitted radiation; detecting the second transmitted radiation at a detector positioned a second distance from the second radiation source, wherein the path traveled by the second transmitted radiation through the tissue creates a second mean radiation path; determining an overlap absorbance between the first mean radiation path and the second mean radiation path; repeating the steps of delivery of the first radiation, the detection of the first transmitted radiation, the delivery of the second radiation, the detection of the second transmitted radiation and the determining of the overlap absorbance using a plurality of first radiation sources and a plurality of second radiation sources to create a plurality of overlap absorbances; and mapping the plurality of overlap absorbances on a coordinate plane, wherein the mapped absorbances create a map of oxygenated and deoxygenated regions of hemoglobin in the tissue over time.

In another embodiment, a system for tissue imaging can include a support comprising a first surface and configured to support a plurality of devices in proximity to a tissue, the tissue comprising both oxygenated and deoxygenated hemoglobin; a plurality of radiation sources positioned on the first surface, the radiation sources configured to deliver a first radiation of a first wavelength range to the tissue, the first wavelength range including wavelengths between about 650 nm and about 1000 nm, wherein the tissue absorbs at least a portion of the first radiation; and deliver a second radiation of a second wavelength range to the tissue, the second wavelength range including wavelengths between about 650 nm and about 1000 nm, the second wavelength range partially overlapping the first wavelength range, wherein the tissue absorbs at least a portion of the second radiation; a plurality of detectors positioned at a first interval on the first surface of the support, the plurality of detectors configured to detect a back-scattered portion of the first radiation and a back-scattered portion of the second radiation; and provide a signal regarding each of the wavelengths detected; and a control device configured to control the radiation sources such that the first radiation and the second radiation is delivered in a multiplexed fashion; determine an amount of absorption by the tissue from each of the first radiation and the second radiation using the intensity of the back-scattered portion of the first radiation and the intensity of the back-scattered portion of the second radiation; determine a location of absorption in the tissue using the position of the first radiation source and the second radiation source in relation to the detector; and create a map of oxygenated and deoxygenated hemoglobin in the tissue using the amount of absorption and the location of absorption.

In another embodiment, an imaging device can include a near infrared spectroscopy (NIRS) device having a support comprising a first surface; a plurality of radiation sources positioned in connection with the first surface; a plurality of radiation detectors positioned in connection with the first surface; a processor in connection with the near infrared spectroscopy device; and a non-transitory memory adapted to store a plurality of machine-readable instructions. The plurality of machine-readable instructions can, when executed by the processor, cause the imaging device to create a volumetric map, the dimensions of the volumetric map corresponding to the tissue portion; subdivide the volumetric map into volumetric subregions, the volumetric subregions comprising a plurality of voxels, each voxel being assigned either preassigned values or random values; overlay a sensitivity map onto the volumetric map, the sensitivity map having a photon migration pattern; perform at least one iterative cycle; and repeat the iterative cycle until either a preset maximum is reached or the measurement error is less than a present threshold.

The iterative cycle can include determining the measurement array and the calculated array for the volumetric map, the measurement array comprising optical measurements corresponding to the photon migration pattern, the calculated array comprising determined measurements corresponding to the assigned value as weighted by the photon migration pattern; increasing an assigned value of a test voxel of the volumetric map, each of the test voxel being selected from the voxels of the volumetric subregions, the increase perturbing the volumetric map; calculating perturbed determined measurements of a perturbed calculated array for the volumetric map; and determining an error between the measurement array and the perturbed calculated array of the volumetric map, wherein if the perturbation causes the error to go down, then a volumetric Gaussian kernel having a radius is centered on the test voxel and extending to a plurality of proximate voxels, the test voxel and the proximate voxels being permanently increased in perfusion proportionally to the magnitude of the error decrease multiplied by a proportional factor A, and wherein if the perturbation causes the error to go up, then a volumetric Gaussian kernel having a radius is centered on the test voxel and extending to a plurality of proximate voxels, the test voxel and the proximate voxels being permanently decreased in perfusion proportionally to the magnitude of the error increase multiplied by a proportional factor A.

In another embodiment, a method for tissue imaging in a transplanted tissue can include positioning a near infrared spectroscopy (NIRS) device in connection with a tissue portion located on a donor location of a first body, the NIRS device being positioned for a near infrared measurement; collecting a first NIRS measurement using the NIRS device, the first NIRS measurement providing volumetric information regarding blood oxygenation or tissue perfusion; removing the tissue portion from the donor location of the first body; transplanting the tissue portion to a recipient location of the first body or a second body; collecting a second NIRS measurement, the second NIRS measurement providing volumetric information regarding blood oxygenation or tissue perfusion; and comparing the first NIRS measurement to the second NIRS measurement to determine a change in blood oxygenation or tissue perfusion.

In another embodiment, a system for tissue imaging can include a near infrared spectroscopy (NIRS) device having a support comprising a first surface and configured to support a plurality of devices in proximity to a tissue, the tissue comprising both oxygenated and deoxygenated hemoglobin; a plurality of radiation sources positioned on the first surface; and a plurality of radiation detectors positioned in connection with the first surface; and a control device having a processor in connection with the NIRS device; and a non-transitory memory adapted to store a plurality of machine-readable instructions.

The radiation sources can be configured to deliver a first radiation of a first wavelength range to the tissue, wherein the tissue absorbs at least a portion of the first radiation; and deliver a second radiation of a second wavelength range to the tissue, the second wavelength range partially overlapping the first wavelength range, wherein the tissue absorbs at least a portion of the second radiation. The plurality of detectors can be configured to detect a back-scattered portion of the first radiation and a back-scattered portion of the second radiation; and provide a signal regarding each of the wavelengths detected.

The plurality of machine-readable instructions can, when executed by the processor, cause the near infrared spectroscopy device to create a volumetric map, the dimensions of the volumetric map corresponding to the tissue portion; subdivide the volumetric map into volumetric subregions, the volumetric subregions comprising a plurality of voxels, each voxel being assigned either preassigned values or random values; overlay a sensitivity map onto the volumetric map, the sensitivity map having a photon migration pattern; perform at least one iterative cycle; and repeat the iterative cycle until either a preset maximum is reached or the measurement error is less than a present threshold.

The iterative cycle can include determining the measurement array and the calculated array for the volumetric map, the measurement array comprising optical measurements corresponding to the photon migration pattern, the calculated array comprising determined measurements corresponding to the assigned value as weighted by the photon migration pattern; increasing an assigned value of a test voxel of the volumetric map, each of the test voxel being selected from the voxels of the volumetric subregions, the increase perturbing the volumetric map; calculating perturbed determined measurements of a perturbed calculated array for the volumetric map; and determining an error between the measurement array and the perturbed calculated array of the volumetric map, wherein if the perturbation causes the error to go down, then a volumetric Gaussian kernel having a radius is centered on the test voxel and extending to a plurality of proximate voxels, the test voxel and the proximate voxels being permanently increased in perfusion proportionally to the magnitude of the error decrease multiplied by a proportional factor A, and wherein if the perturbation causes the error to go up, then a volumetric Gaussian kernel having a radius is centered on the test voxel and extending to a plurality of proximate voxels, the test voxel and the proximate voxels being permanently decreased in perfusion proportionally to the magnitude of the error increase multiplied by a proportional factor A.

BRIEF DESCRIPTION OF THE DRAWINGS

So that the manner in which the above recited features of the present inventions can be understood in detail, a more particular description of the inventions, briefly summarized above, may be had by reference to embodiments, some of which are illustrated in the appended drawings. It is to be noted, however, that the appended drawings illustrate only typical embodiments of this inventions and are therefore not to be considered limiting of its scope, for the inventions may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments disclosed herein generally relate to methods devices and systems for visualization of blood flow and oxygenation in any living tissue. The device described here uses near infrared (NIR) radiation at a plurality of points through a probe in contact with the skin to produce a three dimensional map of blood flow and oxygenation. A map of the blood flow and oxygenation is created using the detected absorption of the NIR radiation. The methods, devices and systems described herein can detect both the existence and location of arterial occlusions, venous occlusions and other alterations of normal perfusion during a surgical procedure and in a non-invasive fashions. Further, the images forming the map can be produced at real-time intervals, such as every second or less.

In addition to the above scope of utility, this imaging system has wide utility in the assessment of tissue viability in many other scenarios, such as compartment syndrome (after a leg crush injury, for example) and even intraoperative assessment of organ tissue viability during certain surgical procedures.

The NIRS device can be placed in contact with the skin of the subject. The NIRS device delivers the NIR radiation several centimeters beneath the skin. A portion of the NIR radiation is then back-scattered back toward the surface where it is detected by a plurality of radiation detectors, such as photodetectors. This back-scattered radiation provides information about the absorbance within a specific area of the tissue and can be used to produce a color coded map of the perfusion of the targeted tissue. The color coded volumetric map, which can be a perfusion map or an oxygenation map, is generated using the back-scattered radiation as an indication of the absorbed wavelengths in each portion of the tissue. The wavelengths are absorbed differently by oxygenated and deoxygenated hemoglobin. The absorption intensity and location provide a pattern based on the oxygenation state of the hemoglobin, which can be incorporated into a three dimensional (3D) map to visualize the oxygenation and deoxygenation of hemoglobin in the tissue. The embodiments disclosed herein are more clearly described with reference to the figures below.

Figure 1A:
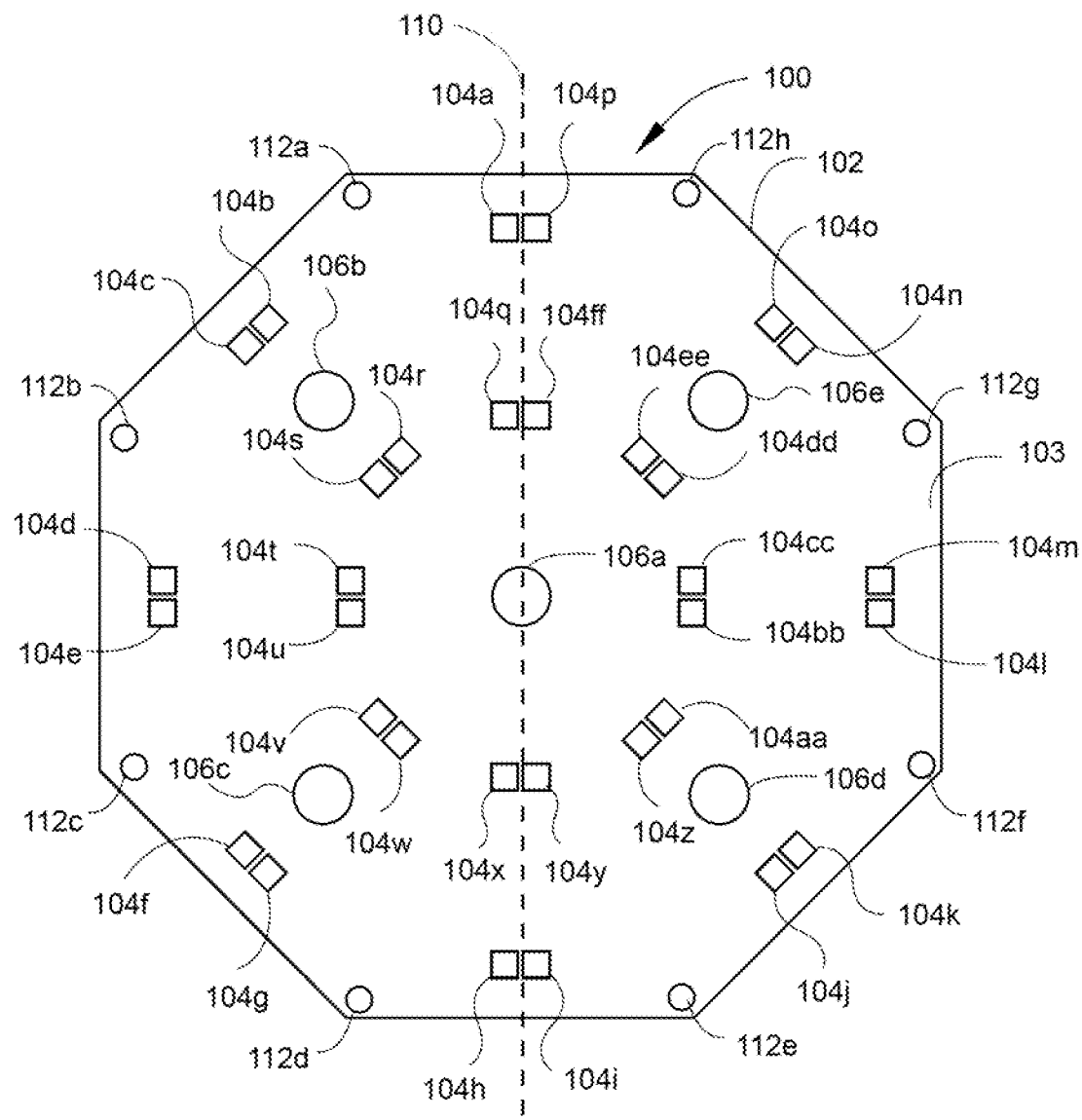
FIG. 1A depicts a top view of a device according to an embodiment disclosed herein.

FIG. 1A depicts a top view of a NIRS device 100 according to an embodiment. The NIRS device 100 includes a support 102 which supports a plurality of additional components of the NIRS device 100. The support 102 can be made of a material used in electronic devices, such as silicon, germanium or other suitable materials. In one embodiment, the support 102 is a standard circuit board. The support 102 may be flexible or rigid. The support 102 may be of a shape and size to accommodate the area being probed and the needs of the user or the subject. The support 102 shown here is an octagonal shape. However, the support 102 can be a circle, a square, a triangle, combinations thereof or permutations thereof. The support has a first surface 103 and a second surface (not shown) opposite the first surface. The first surface 103, though depicted as flat, may be flat, curved, wavy or other shapes as needed or desired by the user or the subject.

The support 102 can have a plurality of radiation sources 104a-104ff. The radiation sources 104a-104ff can be any available source of radiation, such as a light emitting diode (LED), a laser source or other radiation sources. Further, the radiation sources 104a-104ff can be light delivery devices in connection with a radiation source, such as a fiberoptic wire in connection with a radiation source listed above. The radiation sources 104a-104ff can be discrete components which are positioned on the support 102 or the radiation sources 104a-104ff can be integrated into the support 102. In this embodiment, the radiation sources 104a-104ff are integrated into the support 102. The radiation sources 104a-104ff can be positioned anywhere on the surface of the support. Here, the radiation sources 104a-104p form a first circle with a center at the center of the support 102 and radiation sources 104q-104ff form a second circle which is concentric with the first circle.

The plurality of radiation sources 104a-104ff can be separated into a set, shown here as sixteen (16) groups of two. For example, radiation source 104b and radiation source 104c are part of a set. However, larger sets of the plurality of radiation sources 104a-104ff are possible. For clarity of discussion, the radiation sources 104b, 104d, 104f, 104h, 104j, 104l, 104n, 104p, 104r, 104t, 104v, 104x, 104z, 104bb, 104dd and 104ff can also be referred to as the first radiation sources of the set and the radiation sources 104a, 104c, 104e, 104g, 104i, 104k, 104m, 104o, 104q, 104s, 104u, 104w, 104y, 104aa, 104cc and 104ee can also be referred to as the second radiation sources of the set. The first radiation sources of each set can be positioned in close proximity or adjacent to the second radiation sources of the set. Further, the first radiation sources and the second radiation sources of each set can be equidistant from one or more of the detectors 106a-106e. For example, the radiation source 104d and the radiation source 104e are equidistant from the detector 106a. This positioning will allow two separate wavelengths or ranges of wavelengths to be delivered over largely the same area such that the absorption patterns can be determined and mapped.

The radiation sources 104a-104ff can produce radiation at wavelengths from about 650 nm to about 1000 nm. At least one radiation source of each of the sets of radiation sources produces a range of radiation wavelengths. The range of radiation wavelengths has at least a portion of the wavelengths between about 650 and about 1000 nm, such as between about 800 nm and about 950 nm. In one embodiment, at least one of the radiation sources of the set of radiation sources produces a range of radiation wavelengths including a wavelength of 880 nm. Shown here, the radiation sources 104b, 104d, 104f, 104h, 104j, 104l, 104n, 104p, 104r, 104t, 104v, 104x, 104z, 104bb, 104dd and 104ff (the first radiation sources of the set) produce radiation between about 650 nm and about 1000 nm. Further, at least one of the plurality of radiation sources 104 produces a range of radiation wavelengths. The range of radiation wavelengths has at least a portion of the wavelengths between about 650 and about 1000 nm, such as between about 650 and about 800 nm. In one embodiment, at least one of the radiation sources of the set of radiation sources produces a range of radiation wavelengths including a wavelength of about 660 nm. The radiation sources 104a, 104c, 104e, 104g, 104i, 104k, 104m, 104o, 104q, 104s, 104u, 104w, 104y, 104aa, 104cc and 104ee (the second radiation sources of the set) produce radiation from about 650 and about 1000 nm. In this embodiment, the first radiation sources of each set produce at least one wavelength which is not produced by the second radiation sources of the respective set. In one example, the radiation source 104b produces at least one radiation wavelength which is different from the radiation source 104c.

The support 102 can further include one or more detectors 106a-106e. The detectors 106a-106e can be any device which detects one or more wavelengths of radiation. The detectors 106a-106e may be photodetectors, such as a photoconductor, a junction photodetector, avalanche photodiodes, other types of detectors which can directly detect radiation, indirectly detect radiation or combinations thereof. The detectors 106a-106e can be discrete components which are positioned on the support 102 or the detectors 106a-106e can be integrated into the support 102.

Figure 1B:
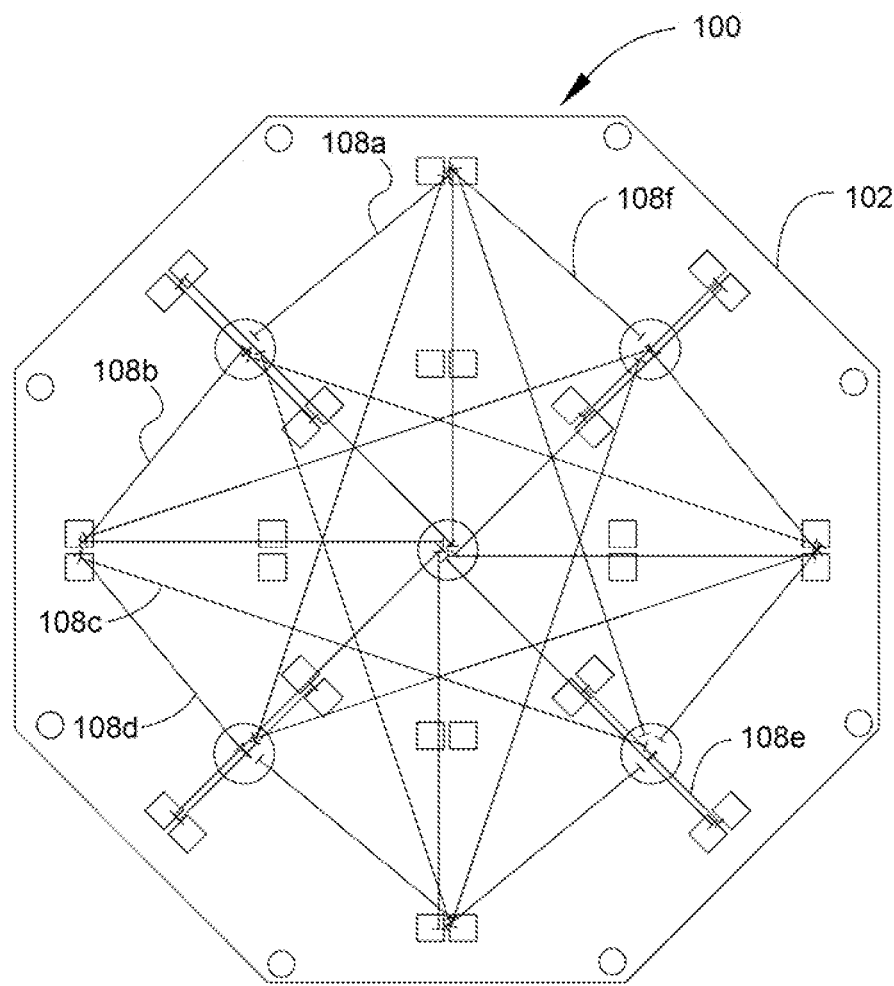
FIG. 1B depicts the device with the plurality of interdistances according to one embodiment disclosed herein.

FIG. 1B depicts the NIRS device 100 with the plurality of interdistances according to one embodiment disclosed herein. The interdistance in the space between one of the plurality of radiation sources 104a-104ff and one of the plurality of detectors 106a-106e. As the radiation delivered from each of the radiation sources 104a-104ff will diffuse in the tissue in all directions, each of the detectors 106a-106e will receive some radiation from each of the radiation sources 104a-104ff. Therefore, the positioning of the plurality of detectors 106a-106e and the plurality of radiation sources 104a-104ff creates a web of interdistances, exemplified here as interdistances 108a-108f. To maintain clarity, not all interdistances are shown in FIG. 1B.

Figure 1C:
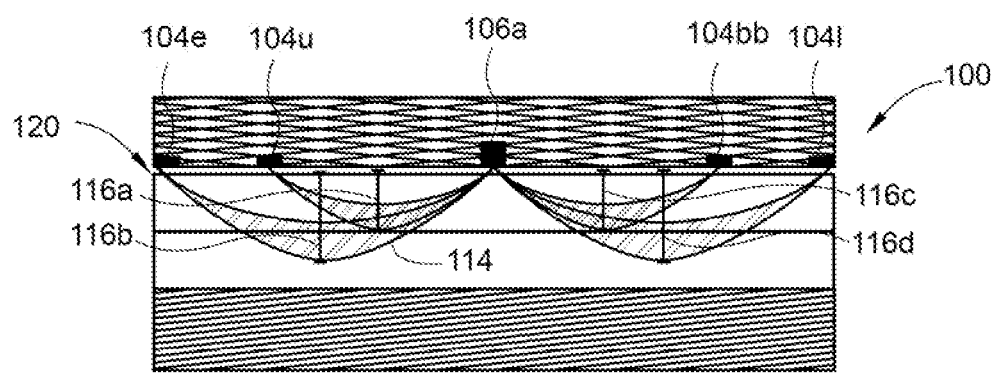
FIG. 1C depicts a side view of the device positioned in connection with a tissue according to an embodiment disclosed herein.

In FIG. 1C, the NIRS device 100 can be positioned in proximity to a tissue 120. The tissue 120 can be a human tissue, such as that which is transplanted or grafted during reconstructive surgery. In this side view, only detector 106a and radiation sources 104e, 104u, 104bb, and 104l are visible, The detector 106a and radiation sources 104e, 104u, 104bb, and 104l are positioned on the support 102 with a specific interdistance between them. It is believed that the main determinant of the detection depth 116, when composition of the tissue 120 is not considered, is the interdistances between the radiation source and the detector, such as the interdistance between the radiation sources 104e, 104u, 104bb, and 104l and the detector 106a. Radiation that happens to travel close to the surface of the tissue 120 is very likely to be lost out of the tissue 120 before reaching the detector. Thus, interdistance between the radiation source and the detector will not detect most of the radiation which travels close to the surface except in the portion of the tissue 120 directly under the radiation sources 104e, 104u, 104bb, and 104l and the detector 106a. On the other hand, radiation which is not sufficiently scattered, radiation which is scattered in other directions or radiation which is absorbed by the tissue 120 is not returned to the detector 106a. The remaining radiation, excluding the lost radiation between the radiation source 104 and the detector 106 and the distant radiation which does not return to the detector 106, create a mean radiation path 114 in an arcuate shape shown in FIG. 1C. By modulating the interdistance between the radiation source 104 and the detector 106, the average detection depth 116 can also be modulated.

Radiation between about 650 nm and about 1000 nm can be used to identify the position and quantity of hemoglobin in the tissue 120. Hemoglobin has a wide absorbance range, for both the HHb and $HbO_2$ states, in the range of about 650 nm to about 1000 nm. The isosbestic point between HHb and $HbO_2$ is about 808 nm. The isosbestic point is a specific wavelength at which two chemical species have the same molar absorptivity. Thus, HHb is the primary absorbing component in the range of between about 650 nm to about 808 nm and $HbO_2$ is the primary absorbing component in the range of between about 808 nm and about 1000 nm. At wavelengths below 650 nm, the absorption of hemoglobin is too high which would prevent anything but superficial measurement of the specific subtype. At wavelengths above 1000 nm, the absorption of water is too high which would prevent measurement of absorption of either HHb or $HbO_2$. Using the absorbance ranges described above, the overall quantity of hemoglobin in an area can be determined while differentiating between HHb and $HbO_2$ in the same area.

As described above, the interdistance between one of the radiation sources 104 and one of the detectors 106 can be used to increase or decrease the detection depth 116a-116d. It is further believed that the detection depth 116a-116d at the midpoint between one of the detectors 106 and one of the radiation sources 104 is approximately ⅔ of the interdistance between the detector 106 and the radiation source 104. The positioning of the radiation sources 104 and the detectors 106 creates a plurality of mean radiation paths 114. The mean radiation paths 114 are the average path for radiation through the tissue 120, which penetrates to various depths and overlaps with other mean radiation paths 114. The information provided by the mean radiation paths 114 and their overlap can be used to create the three dimensional map of the HHb and the $HbO_2$ as well as to differentiate between the comparative concentrations thereof, described more clearly with reference to FIGS. 3A and 3B.

A plurality of vacuum ports 112, shown in FIG. 1A, can be formed in the support 102. The vacuum ports 112 can be connected with a vacuum supply (not shown). The vacuum ports 112 may be of various sizes and shapes, such as the eight circular vacuum ports 112 shown here. The vacuum ports 112 may be formed at the edges of the support 102 or at an internal portion of the surface 103. The vacuum ports 112 may be used to apply a vacuum to an underlying surface, such as the surface of the tissue 120, thus creating a more secure connection between the surface 103 and the tissue 120. In further embodiments, the vacuum ports 112 are omitted and the NIRS device is secured to the tissue 120 using other means, such as through the use of adhesives or bandages.

The distance between the NIRS device 100 and the tissue 120 should be minimized to minimize reflection of the radiation from the surface of the tissue 120. A media interface, such as that which forms at the surface of the tissue 120 in the presence of atmospheric gases, can create a partially reflective surface to the NIR radiation. Reflection from an interface surface is a function of the distance from the surface, as radiation diffuses over a distance in atmosphere. Thus, the surface of the tissue 120 reflects a higher proportion of the wavelengths of NIR radiation when the tissue 120 is spaced a greater distance from the radiation sources 104a-104ff. By decreasing the distance between the radiation sources 104a-104ff and the tissue 120, either with or without the vacuum ports 112, the effect of reflection at the interface is diminished.

Though, the NIRS device 100 and the related methods and technological advances are depicted in the context of a specific tissue, such as the skin, the scope of the embodiments disclosed herein are not limited to any specific tissue. The scope of the methods or devices disclosed herein can easily be modified to accommodate other forms of organ surgery and in vivo applications. In one embodiment, the NIRS device 100 as described herein, can provide real-time, 3-D volumetric mapping technology intraoperatively to image hearts coming off of bypass. Thus, the NIRS device 100 allows a clinician to assess the adequacy of coronary sufficiency. In another embodiment, the NIRS device 100 can be used to image renal tissue during partial nephrectomy with intraoperative vascular occlusion. In another embodiment, the NIRS device 100 can be applied to various types of hepatic and neurosurgical procedures. Additionally, given that the imaging system has the ability to penetrate through a few centimeters of tissue, non-operative (external to the body/non-invasive) muscle mapping during exercise (or as a response to exercise) can be envisioned to aid in athletic performance and rehabilitation medicine. Oxidative information provided by the NIRS device 100 can be applied following a stroke or other types of physical compromise.

Additionally, the NIRS device 100 may be incorporated into other devices, such that a first device incorporates the functionality of the NIRS device 100 as described herein. In one embodiment, the NIRS device 100 is incorporated into surgically implanted devices, such as automatic defibrillators, pacemakers, stimulators and the like, to transcutaneously transmit organ tissue perfusion on a periodic basis. One or more wireless communication methods or protocols can then be incorporated to receive the information transmitted by the NIRS device 100. For example, the oxygenation information could be sent via bluetooth or other method to a computing device, such as smartphone, a tablet or a laptop. The computing device can then relay the information to a third party, such as the patient, the patient's provider or another clinician.

Figure 1D:
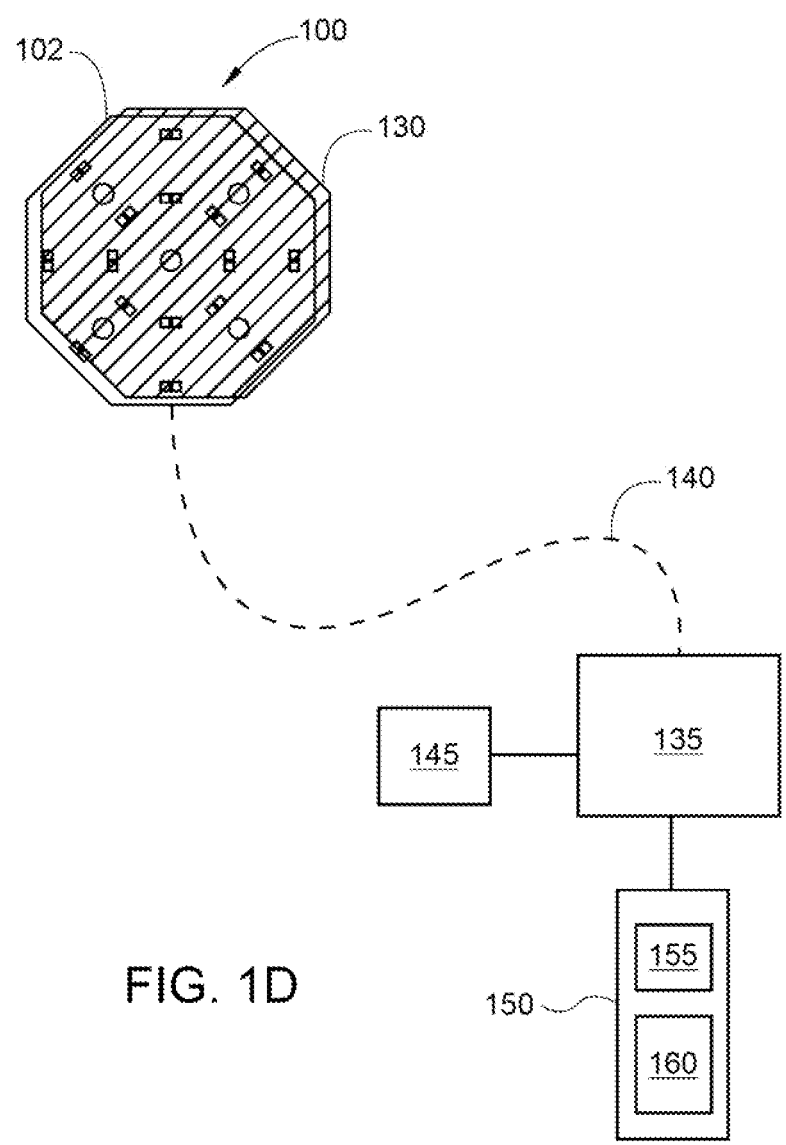
FIG. 1D depicts the device in connection with a data collection unit, according to one embodiment disclosed herein.

FIG. 1D depicts the NIRS device 100 in connection with a data collection unit 135 and a control unit 150, according to an embodiment disclosed herein. The NIRS device 100 can be connected with the data collection unit 135 through the connection 140. The data collection unit 135 can be a single device or a plurality of devices configured to receive and process the information collected by NIRS device 100. The connection 140 between the data collection unit 135 and the NIRS device 100 may be either a wired or wireless connection. The connection 140 shown here is a wired connection.

The data collection unit 135 can be in connection with further devices, such as a control unit 150. In some embodiments, the data collection unit 135, the control unit 150, the NIRS device 100 or combinations are the same device or device component. The combination of the NIRS device 100, the data collection unit 135 and the control unit 150 may be referred to as an imaging device. The control unit 150 can include a processor 155 and memory 160. The control unit 150 can be configured to collect, process or otherwise utilize the received data at the data collection unit 135. The control unit 150 can deliver automated or user-input instructions to the NIRS device 100 to perform one or more of the functions described with reference to FIG.

1A-1C. The control unit 150 can also be a smartphone, an interactive display or other devices. In another embodiment, the data collection unit 135 is a computer including a processor and memory with instructions which, when processed by the computer, causes the computer to perform one or more of the functions described herein. The data collection unit 135 is connected with a power supply 145, which powers the data collection unit 135, the NIRS device 100, the control unit 150 or combinations thereof. The data collection unit 135 can also be connected with further devices through a wireless transmitter. In one embodiment, the data collection unit 135 provides information collected by the NIRS device 100 to a nursing station down the hall, a doctor's office or a call center. Using the control device 150, the data collection unit 135 or both, an individual (e.g., a doctor or a nurse) can track changes in tissue perfusion in near real time, and call the patient back for assessment, surgery or other intervention.

The processor can be a general use processor, as known in the art. Further, the processor can be designed for the specific functions that are disclosed herein. The processor can be designed or configured to perform one or more operations related to the detection of a near infrared signal or for the determination of oxygenation in a tissue. The operations may be represented as instructions in a machine-readable format that are stored on the memory. The memory can be one or more non-transitory types of computer readable media, such as solid state memories, hard drives, and the like. The instructions may reside completely, or at least partially, within the memory and/or within the processor during execution.

In further embodiments, the NIRS device 100 can be coated a coating 130. The coating 130 can be an optically clear biocompatible material, such as silicon. The coating 130 can prevent direct contact between the tissue 120 and electronic components without compromising the functionality due to light reflections.

Figure 2:
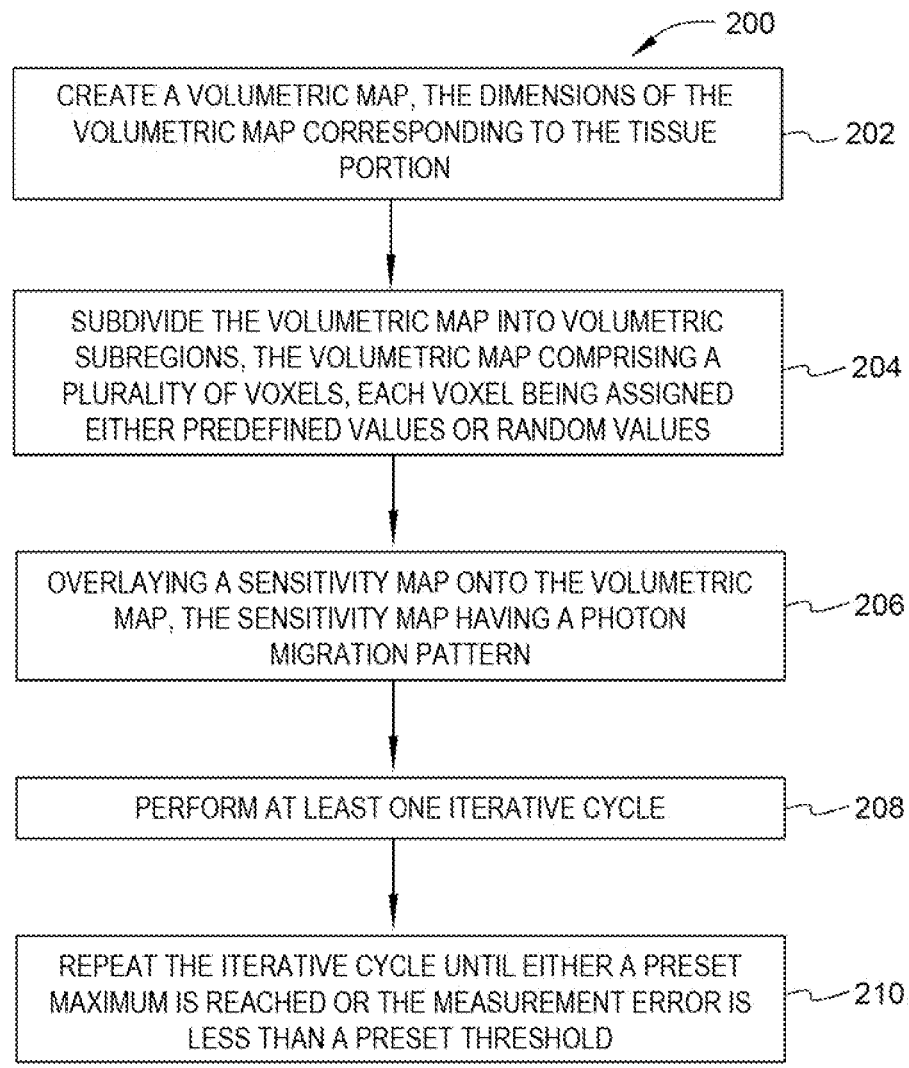
FIG. 2 is a block diagram of machine-readable instructions for processing near infrared spectroscopy information, according to one embodiment.

FIG. 2 is a block diagram of machine-readable instructions 200 for processing near infrared spectroscopy information, according to one embodiment. The memory can be adapted to store a plurality of machine-readable instructions. The machine-readable instructions 200 can, when executed by the processor, cause the imaging device to create a sensitivity map of a tissue portion, the sensitivity map showing a photon migration pattern for the tissue portion; create a volumetric map, the dimensions of the volumetric map corresponding to the tissue portion; subdivide the volumetric map into volumetric subregions, the volumetric subregions comprising a plurality of voxels, each voxel being assigned either preassigned values or random values; overlay the photon migration pattern of the sensitivity map onto the volumetric map; perform at least one iterative cycle; and repeat the iterative cycle until either a preset maximum is reached or the measurement error is less than a present threshold.

Instructions 200 can further include creating a volumetric map, the dimensions of the volumetric map corresponding to the tissue portion, at 202. The volumetric map is the same volume as the tissue portion being examined by the NIRS device. The volumetric map begins with no information incorporated. The volumetric map consists of a plurality of voxels. The voxels are defined regions of the volumetric map representing the smallest distinguishable detection area in the volumetric map.

Instructions 200 can further include subdividing the volumetric map into volumetric subregions, at 204. In one embodiment, the volumetric map is further divided into volumetric subregions. The volumetric subregions are defined three dimensional regions in the volumetric map. The volumetric subregions can be non-overlapping. Further, the volumetric subregions can share common boundaries, such that 100 percent of the volumetric subregions is equivalent to 100 percent of the volumetric map. Stated another way, the volumetric subregions can be composed of the plurality of voxels. The volumetric subregions can be formed such that the boundary of the volumetric subregion does not subdivide a voxel. The number of sub-regions can be fixed or can be dynamically changed throughout the algorithm. In one embodiment, the volumetric subregions are dynamically changed by the exclusion of a determined sub-region, such that the process focuses on sub-regions which have not yet been determined. In another embodiment, the volumetric subregions are dynamically changed by changing the position of the boundaries of the defined subregions, such that either the shape of the subregions change, the position of the subregions change or the number of subregions change.

Instructions 200 can further include assigning each voxel with either preassigned values or random values. As each voxel corresponds to a portion of the tissue, it also has a volumetric value, such as an oxygenation value, that describes or relates to the detected parameter in the corresponding portion of tissue. As it is not currently feasible to deliver radiation to each voxel individually and detect the related absorbance, information must be extrapolated from the optical measurement and onto the voxels of the volumetric map. The program described herein extrapolates this information by providing an assumed volumetric value for each of the voxels, based on either a predefined number or a random number. Possible volumetric values include optical absorption measurements, corresponding readings of concentration of hemoglobin in various states, such as oxyhemoglobin ($HbO_2$) and deoxyhemoglobin (HbB), or other entries which correlate to an optically measurable tissue data.

Instructions 200 can further include overlaying a sensitivity map onto the volumetric map, the sensitivity map having a photon migration pattern, at 206. It is beneficial to know where the photons migrate within the tissue of interest, given the superficial location of all sources and detectors. Specifically, the photon path between each source and each detector of the probe can be determined and then superposed for all source-detector pairs, so to obtain a volumetric map that describes the density of photons in all locations within the tissue. This is called the sensitivity map. The sensitivity map is intended as the map that indicates which sub-regions of tissue, and which voxels, are more sensitive to the detection of a physiological change. The sensitivity is due to a higher density of photons travelling in those regions. In contrast, physiological changes in regions of the tissue where there is no photon travelling will not be directly measurable by optical absorption (i.e., region of the sensitivity map that has a null sensitivity). The sensitivity map relates to the geometric layout of light sources and detectors and to the anatomical properties of the tissue being investigated.

The reconstruction of a volumetric map of blood perfusion or changes thereof can be described as an inverse problem. An inverse problem is a problem where the effect of a physiological phenomenon is known (e.g., by taking single or multiple measurements at any given point in time, for a single or multiple points in time) and a description of the originating phenomenon (e.g., the quantity of oxyhemoglobin ($HbO_2$) and deoxyhemoglobin (HbB)) is sought as a result. As opposed to the "forward problem" (which is calculating the measurable effect of a known originating phenomenon), the inverse problem is substantially more difficult to solve, mainly because a dense representation of the source (in one example, a perfusion image consisting of thousands of voxels) is attempted starting from sparse measurements of the effect (i.e., few dozens of optical measurements).

One approach to the solution of the inverse problem is iterative approach. The volumetric map is initially defined, as described above, and it is subsequently adjusted over a certain number of iterations, until the volumetric map is deemed to be sufficiently accurate. The strategy for adjusting the map at any step of the iterative cycle is based on the error between the actual measurements of the effect (optical measurements or concentration measurements) and the measurements calculated by solution of the forward problem using the estimated volumetric map. As described here, The sum of the assumed volumetric values are then transformed using the sensitivity map.

If the error has a downward trend during subsequent map adjustments, it means that the applied adjustments to the map are going in the right direction and the volumetric map is converging towards a solution of the inverse problem. If the error has an upward trend during subsequent map adjustments, the applied adjustments are wrong and must be corrected in subsequent iterations. The iterative process ends when the error between the actual and estimated measurement is sufficiently low, indicating that the current estimated volumetric map is in fact originating an effect measurement that is sufficiently close to the actual measurement.

To solve the forward problem, it is necessary to know where the photons migrate within the tissue of interest, given the location of all sources and detectors in the NIRS device. Specifically, the photon migration pattern between each source and each detector of the probe need to be determined. The photon migration pattern can then be superposed for all source-detector pairs, which creates a sensitivity map that describes the density of photons derived from the source in all locations within the tissue portion.

Instructions 200 can further include performing at least one iterative cycle, at 210. The iterative cycle can include determining the measurement array and the calculated array for the volumetric map. The measurement array includes an optical measurement for the areas corresponding to the photon migration pattern in the volumetric map. The calculated array includes a determined measurement of the equivalent migration pattern of the volumetric subregion. The optical measurement is the optical measurement of the radiation delivered from each of the radiation sources to the tissue and received by each of the detectors, as affected by absorbance in the corresponding region of tissue (i.e., the tissue in the photon migration pattern). The optical measurement can be performed as described below with relation to FIGS. 2-3C. The determined measurements is the calculated equivalent to the optical measurement, as calculated from the voxels of the volumetric map which correspond to the photon migration pattern and weighted based on the sensitivity map.

In one embodiment, the measurement is a single measurement for all radiation source/detector combinations. The single measurement can be used throughout all iterative cycles. Each of the measurement array and the calculated array include a number of values related to the total number of radiation source/detector combinations. In one embodiment, there are sixty-four (64) radiation source/detector combinations. Therefore, in this embodiment, there are sixty-four (64) actual optical measurements in the measurement array and 64 determined measurements in the calculated array.

The iterative cycle can further include increasing an assigned value of a test voxel and calculating a perturbed calculated array for the volumetric map, wherein the volumetric map is perturbed at a test voxel within the selected subregion. Using the embodiment described above, a single assigned value is changed for a test voxel. The assigned value can be a perfusion value. The 64 determined measurements for the calculated array are produced from the volumetric map. The 64 determined measurements (i.e., the calculated array) are then compared to the 64 actual optical measurements (i.e., the measurement array) to determine the distance between the values.

Each of the test voxels are selected from the voxels of the volumetric subregions. As stated above, the voxels of the volumetric map are given an assigned value, which can be either arbitrary or predefined. When the test voxel is increased in value, the increase will perturb the value of the measurement corresponding to the volumetric subregion. The perturbed calculated array, which is the sum of the values of the voxels in the volumetric map as transformed by the sensitivity map, can then be calculated for each of the photon migration patterns.

In one embodiment, predefined can mean defined through a previous iterative cycle. The iterative process converges faster when the value assigned to the voxels of the volumetric map at the first iteration is close to the real solution. As such, the algorithm can include the creation of a pre-measurement volumetric map of the tissue. The pre-measurement can have a longer than standard duration (e.g., 10-60 seconds, considering that it starts from a null, or unknown image). The pre-measurement voxel values can then be used to set the initial value of the voxels for future measurements. It is believed that, because the physiological changes occur quite slowly (in the order of tenth of seconds or minutes), that an image calculated at a previous point in time would provide values which approximates the volumetric map at a current point in time. Further, any physiological traits of the tissue portion which affect an oxygenation parameter will be represented to some extent in the pre-measurement volumetric map. As such, by using the individually established values from a pre-measurement for the base value for the voxels in a later iterative cycle, the values will be both more quickly derived and more precise than arbitrary values or preassigned values which are established in another fashion.

The iterative cycle can further include determining the error between each of the optical measurements of the measurement array and the perturbed determined measurement of a perturbed calculated array. The error is determined using the Euclidean distance between the two points P and Q, where P is the measurement array and Q is the calculated array. The Euclidean distance between points P and Q is the distance between the points in an Euclidean space of n-dimensions (n-space). Thus, the distance between the points correlates to the error in the perturbed determined measurements of the perturbed calculated array. In one example, a total of 64 photon migration patterns creates a total of 64 optical measurements for the volumetric map. The 64 optical measurements are the P values, which are compared against the 64 perturbed determined measurements (i.e., the Q values) The distance between these points is the magnitude of the error. In Cartesian coordinates, if $P=(P_1, P_2, \ldots, P_n)$ and $Q=(Q_1, Q_2, \ldots, Q_n)$ are two points in Euclidean n-space, then the distance (d) from P to Q, or from Q to P is given by:

$$d(p, q) = d(q, p)$$
$$= \sqrt{(q_1 - p_1)^2 + (q_2 - p_2)^2 + \ldots + (q_n - p_n)^2}$$
$$= \sqrt{\sum_{i=1}^{n} (q_i - p_i)^2}.$$

If the perturbation causes the measurement error to go down, then a volumetric Gaussian kernel of sigma value S (similar to the radius of a sphere) is centered on the perturbed voxel and is permanently increased in perfusion proportionally to the magnitude of the error decrease multiplied by a proportional factor A. If the perturbation causes the measurement error to go up, then the perfusion map is updated by decreasing the perfusion locally in a volumetric Gaussian kernel of sigma value S and centered on the perturbed voxel and is permanently decreased in perfusion proportionally to the magnitude of the error increase multiplied by a proportional factor A. The machine-readable instructions 200 can be executed sequentially or in a predetermined order.

The sigma value S is an assigned value which corresponds to the radius of the Gaussian kernel from a starting point of the center of the test voxel. The value S is not necessarily a static value and can change throughout the iterations. The proportional factor A is an intensity value which determines the proportion of change in voxel value within the Gaussian kernel. The factor A is not necessarily a static value and can change throughout the iterations. If value of distance (d) is increased from the baseline measurement (e.g., the distance between P and Q based on the measured value and the original assigned value), then the perturbed voxel and surrounding region are adjusted down by an order of magnitude using the above described Gaussian kernel transformation. If this value is decreased from the baseline measurement, then the perturbed voxel and surrounding region are adjusted up by an order of magnitude using the above described Gaussian kernel transformation.

The instructions 200 can further include repeating the iterative cycle until either a preset maximum number of iterations is reached or the measurement error is less than a preset threshold, at 210. The preset maximum is a maximum number of events until number the iterative cycles are deemed to be sufficient. The preset maximum can be a number of iterative cycles, an amount of time or other maximum attributes as defined by the user. The preset threshold is a boundary set for the measurement error. The preset threshold can be less than 5 percent error, such as less than 1 percent error.

Figure 3A:
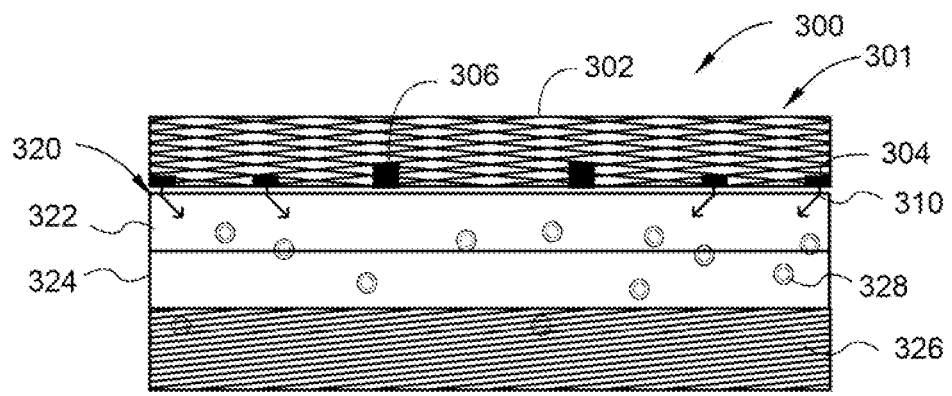
FIGS. 3A-3C depict a system according to an embodiment disclosed herein.
Figure 3B:
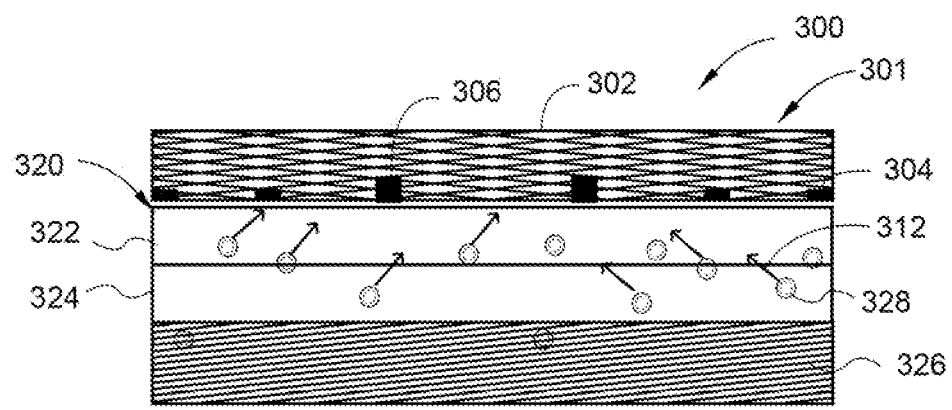
Figure 3C:
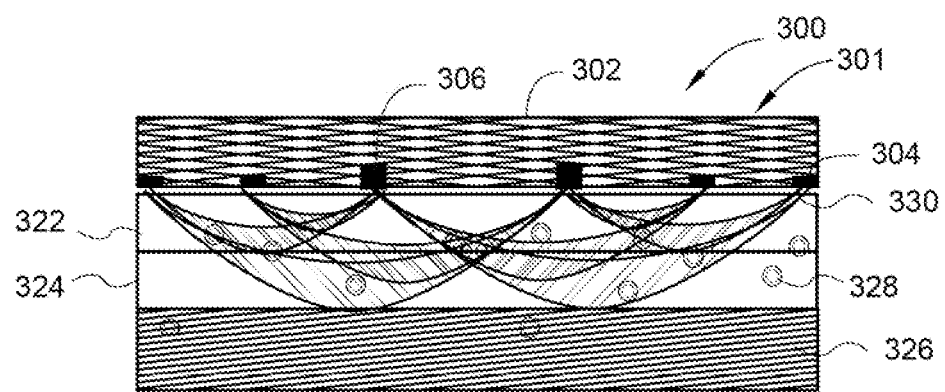

FIGS. 3A-3C depict a NIRS system 300 in operation according to an embodiment disclosed herein. The NIRS system 300 includes a NIRS device 301 with a support 302 with a plurality of radiation sources 304 and a plurality of detectors 306. The radiation sources 304 and the detectors 306 may be substantially the same as the radiation sources 104 and the detectors 106, described with reference to FIGS. 1A and 1B. In FIG. 3A, the radiation sources 304 and the detectors 306 are embedded in the support 302. The NIRS device 301 is positioned in connection with a tissue 320. The tissue 320 can include a plurality of layers, such as a first layer 322, a second layer 324 and a third layer 326. The first layer 322 can be skin layer, the second layer 324 can be an adipose layer and the third layer 326 can be a muscle layer. The first layer 322, the second layer 324 and the third layer 326 may be composed of one or more individual sub-layers (not shown). Further, though the first layer 322, the second layer 324 and the third layer 326 are depicted here as discrete layers, the layers may not form a distinguishable boundary. Hemoglobin 328 may be interspersed in the first layer 322, the second layer 324 and the third layer 326. The hemoglobin 328 can be found in distinct vessels (e.g., arteries, veins, arterioles, venules, and capillary beds) which are interspersed in the first layer 322, the second layer 324 and the third layer 326.

In operation, the radiation sources 304 of the NIRS system 300 produce a NIR radiation 310 which is directed toward the tissue 320. The NIR radiation 310 penetrates the first layer 322, the second layer 324 and the third layer 326. The tissue 320 causes a distortion in the directionality of the NIR radiation 310, based on the scattering property of the tissue. The scattering property of the tissue, including the scattering coefficient, relates to the composition of the tissue 320. Table values can be used to determine the scattering coefficient of specific tissue types which may form the layers of the tissue 320. Further, the scattering coefficient can be determined using other measuring techniques, including optical techniques. If the scattering coefficient is low, the radiation would simply travel through and not reflect, refract or otherwise change direction. Without back-scattering, the NIR radiation 310 would not be received by the detector 306. The layers of the tissue 320, such as skin and adipose tissue, are high scatterers of the NIR radiation 310. As such, part of the NIR radiation 310 is redirected back toward the detector 306. The absorption coefficient is a measured parameter and is determined by the absorption of the NIR radiation 310 by the tissue 320 as a function of the original radiation intensity.

In FIG. 3B, depicts back-scattered radiation 312 returning from the tissue 320. The back-scattered radiation 312 is the NIR radiation 310 of FIG. 3A, as reduced by passing through the tissue 320 and by specific wavelengths at the hemoglobin 328. The back-scattered radiation 312 will be affected by a variety of factors before being received by the detector 306, such as the radiation angle of incidence, tissue type, depth of travel, absorption and the like. The back-scattered radiation 312 will include the wavelengths provided by the radiation source 304 without a portion of the NIR radiation 310 which is absorbed by the hemoglobin 328. The portion of the NIR radiation 310 that is absorbed by the hemoglobin 328 and other factors (such as water and less plentiful chromophores) in relation to the total input of the NIR radiation 310 is used to create the map. The pathway of the NIR radiation 310 and the back-scattered radiation 312, though depicted as linear for clarity, is not necessarily linear. The NIR radiation 310 and the back-scattered radiation 312 will be back-scattered by numerous components of the tissue 320.

In FIG. 3C, the plurality of mean radiation paths 330 between each of the radiation sources 304 and each of the detectors 306 are depicted. These mean radiation paths 330 are an estimate of the paths traveled by the back-scattered radiation 312 in the tissue 320 between each of the radiation sources 304 and each of the detectors 306. The mean radiation paths 330 are based on empirical data collected above, the substance traveled through, the scattering coefficient, the absorption coefficient, simulations of the optical path based on laws of physics and other parameters. As described above, the mean radiation paths 330 incorporate the expected paths of the NIR radiation 310 and the back-scattered radiation 312. The mean radiation paths 330 have an arcuate shape which diverges from the radiation source 304 to reach a maximum width at the midpoint and then converges toward the detector 306. The arcuate shape is also referred to as a banana or canoe-like shape with ends located at the radiation sources 304 and the detectors 306. The back-scattering described in FIG. 3B creates the width found at the midpoint of each of the mean radiation paths 330.

The NIRS system 300 will be configured to calculate the oxygenation value of each volume element of the matrix (also known as a voxel) as a weighted sum of the measured oxygenation of all mean radiation path 330 volumes that each voxel belongs to. The NIRS system 300 will also be configured to process the oxygenation matrix to generate and display topographic and fMRI-like tomographic views of the blood perfusion within the tissue 320. The absorbance at each of the mean radiation paths 330 of each combination of radiation sources 304 and detectors 306 are compared to one another. The absorbance for each of the mean radiation paths 330 is determined in relation to the wavelength absorbed. The absorbance from the overlapping mean radiation paths 330 or derived information from the absorbance is then plotted on a coordinate plane to produce a map.

By determining the area of overlap for the known mean radiation path, a portion of the absorbance for each of the mean radiation paths can be attributed to that portion based on the area of the overlap with consideration of the x, y and z planes. The overlap of the areas of overlap as mapped on the x, y and z planes provides the three dimensional information regarding oxygenation in the tissue. Increased overlap of areas of overlap gives more accurate boundaries for HHb and $HbO_2$, as the absorbances will be different between mean radiation paths 330. For example, comparison of the overlap absorbance of areas of overlap for mean radiation paths 330 with a wavelength range including 660 nm with the overlap absorbance of overlapping mean radiation paths 330 with a wavelength range including 660 nm will provide information on the quantity of HHb in both of the areas of overlap for the mean radiation paths 330. Cross comparison between separate wavelengths, such as a comparison of the overlap absorbance of areas of overlap for mean radiation paths 330 with a wavelength range including 660 nm and the overlap absorbance of areas of overlap for mean radiation paths 330 with a wavelength range including 880 nm, will produce data regarding the positioning of hemoglobin in the two regions as well as the comparative oxygenation in the region of overlap. The comparative absorption data is then mapped in a 3D matrix, such as through the use of the MATLAB software, available from Mathworks, Inc. located in Natick, Mass. A MATLAB algorithm can be used to generate a 3D matrix. The 3D matrix can include all combination of radiation sources 304 and detectors 306 of the NIRS device 300, or a portion thereof.

Figure 4:
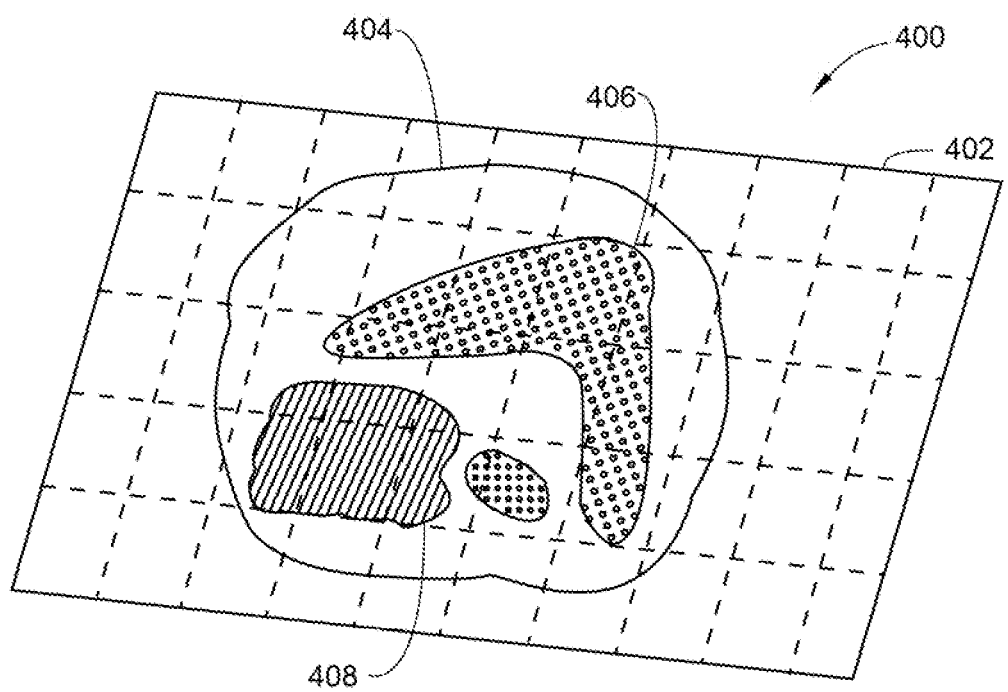
FIG. 4 depicts an example of a slice of the absorbance detected using an NIRS device, according to an embodiment disclosed herein.

FIG. 4 depicts an example of a slice 400 of the absorbance detected using an NIRS device, according to an embodiment disclosed herein. The slice 400 is the mapped absorption on a grid 402 for each of the mean radiation paths produced by an NIRS device at a specific depth. The slice 400 depicts a region 404. The region 404 depicts the boundaries of the detected region, without regard for the presence of HHb or $HbO_2$. The region 404 is determined by the known positioning of the mean radiation paths based on the position of the detectors and the radiation sources for a given tissue. In further embodiments, the region 404 can be determined based on a base line absorbance at one or more of the wavelengths received from the radiation sources. Within the region 404 are deoxygenated areas 408 and oxygenated areas 406. The intensity of the color for the oxygenated areas 406 and deoxygenated areas 408 reflects the level of absorption at a specific wavelength, which will indicate the respective quantities of HHb and $HbO_2$ in the areas. The definition of the boundaries of the oxygenated areas 406 and deoxygenated areas 408 will be dependent on the sample size.

In embodiments where more detectors are used, the clarity of boundaries the oxygenated areas 406 and deoxygenated areas 408 will increase. The oxygenated areas 406 and deoxygenated areas 408 can be further used to determine the boundaries of tissue components, such as venules, arterioles and capillary beds. A three dimensional map can be shown in slices, such as slice 400, by allowing the user to change between depths.

Figure 5:
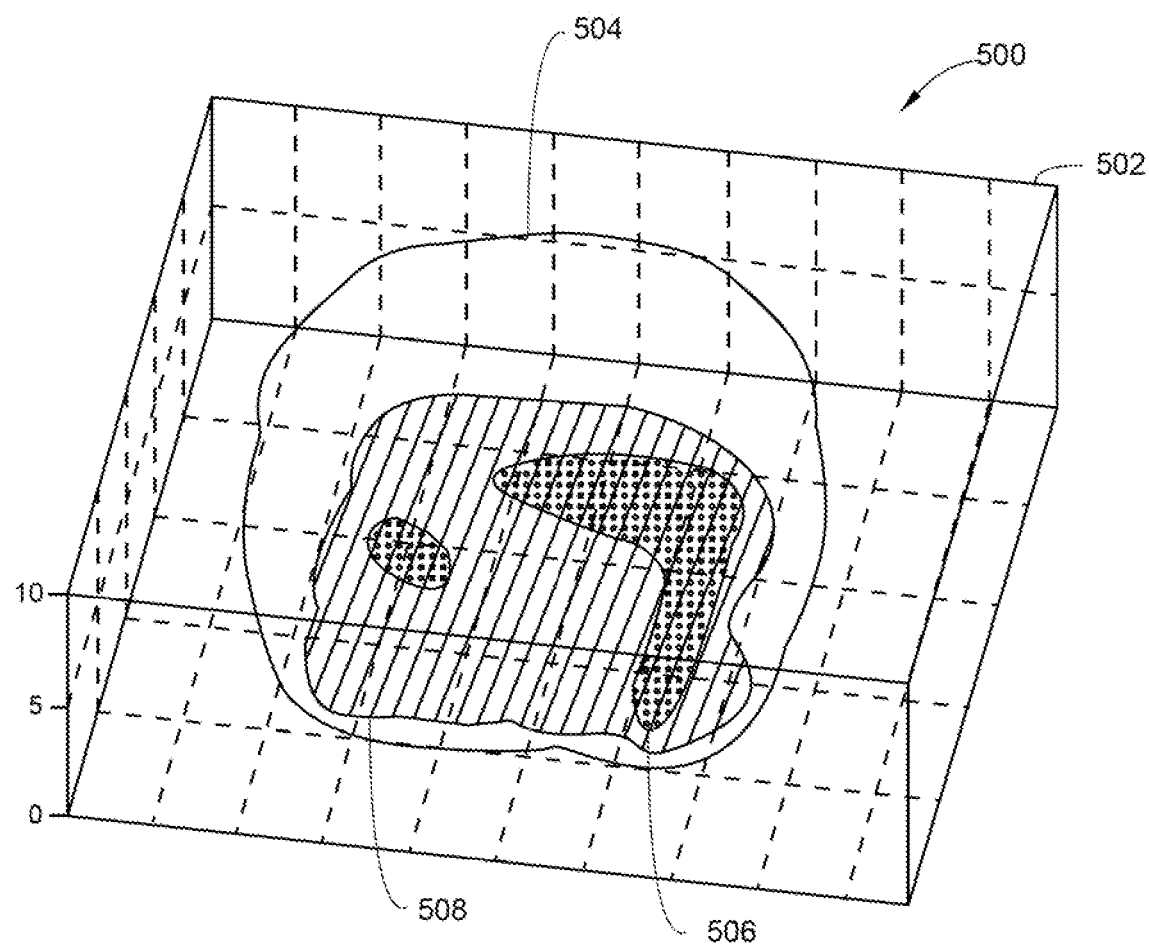
FIG. 5 depicts a map of the absorbance detected using a device, according to an embodiment disclosed herein.

FIG. 5 depicts a map 500 of the absorbance detected using an NIRS device, according to an embodiment disclosed herein. The map 500 is a composite of a plurality of slices, as described above in FIG. 4. The slices are positioned based on depth such that the map 500 provides an three dimensional view. The map 500 includes a 3D grid 502 which provides a frame of reference for the detected absorbances. The region 504 depicts the boundaries of the detected region, without regard for the presence of HHb or $HbO_2$, and is determined based on one or more of the methods described with reference to FIG. 3. Within the region 504 are both oxygenated regions 506 and deoxygenated regions 508. The grid 504 allows for direct comparison based on depth of the specific region, as well as length and width.

Figure 6A:
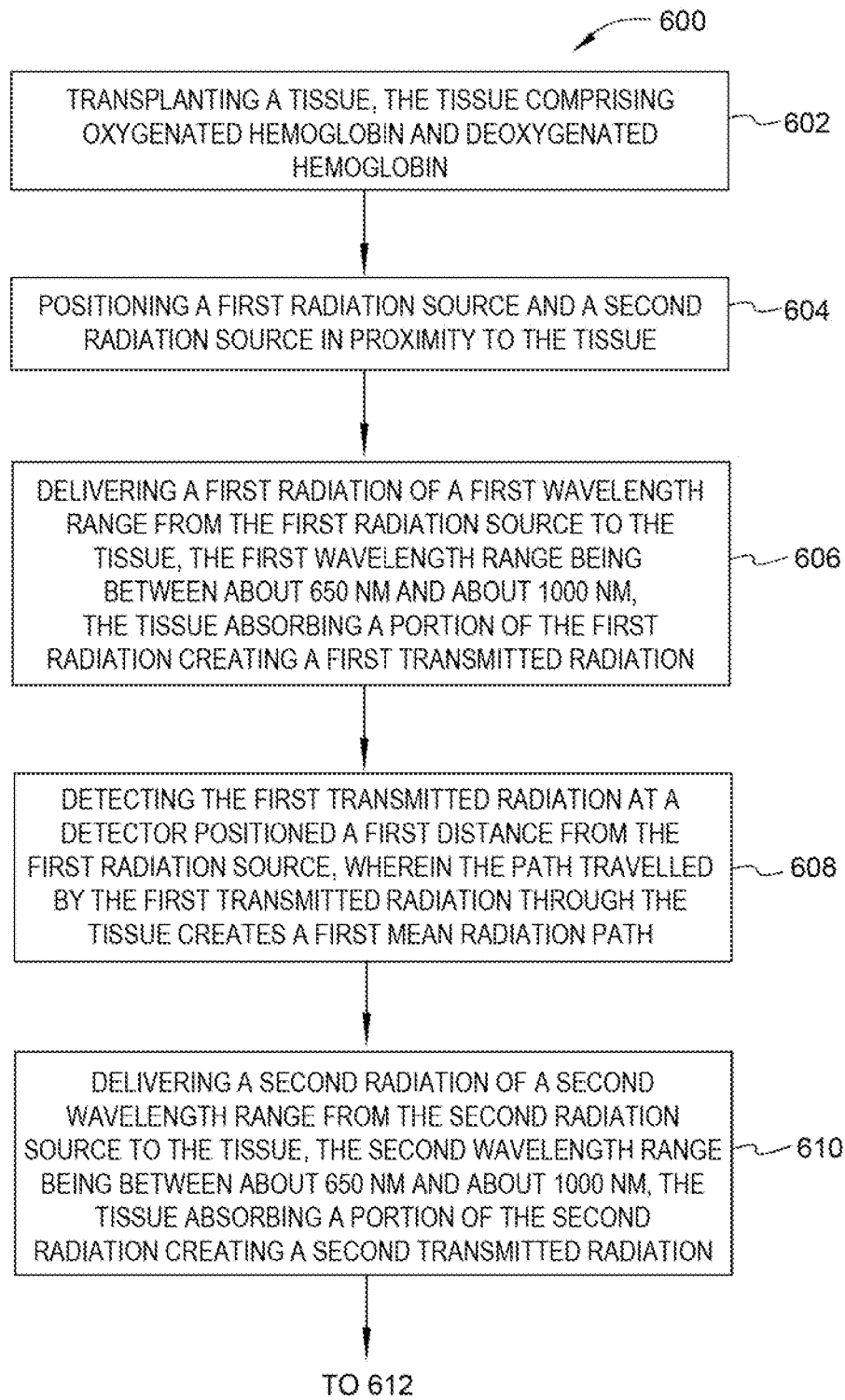
FIGS. 6A and 6B are a flow diagram of a method of mapping perfusion according to an embodiment.
Figure 6B:
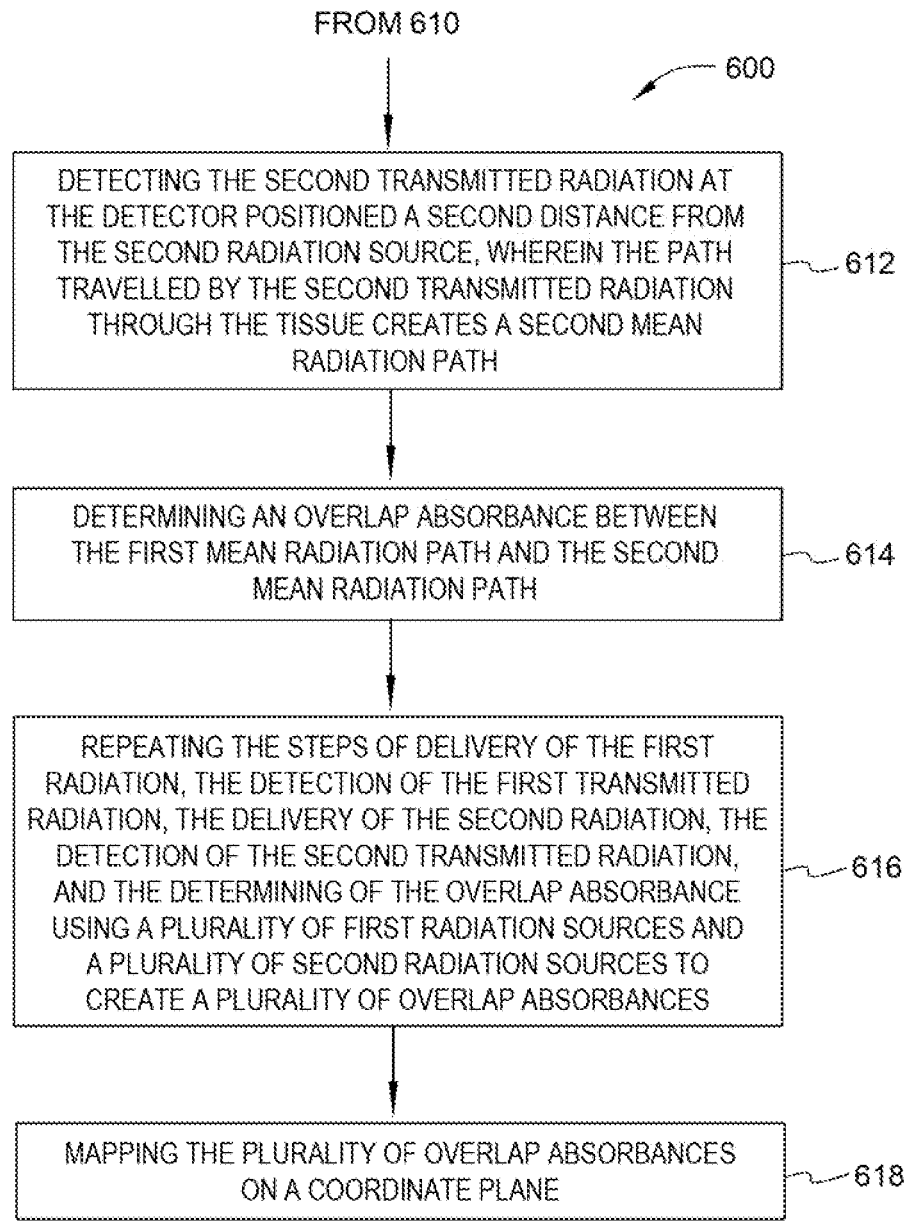

FIGS. 6A and 6B depict a block diagram of a method 600 for determining perfusion of a tissue according to an embodiment disclosed herein. The method 600 can include transplanting a tissue, as in element 602. The tissue comprises both oxygenated and deoxygenated hemoglobin. Generally, the tissue is transplanted from a donor site and is positioned at a location of excised tissue. During the reconstructive process, the transplanted tissue is positioned in connection with the native tissue. Various preexisting arteries, arterioles, veins, venules and capillary beds are reconnected between the native tissue and the tissue transplanted from the donor region. This reconnection assures proper perfusion of the transplanted tissue.

A first radiation source and a second radiation source are positioned in proximity to the tissue, as in element 604. The first radiation source and the second radiation source can be a radiation source as described with reference to FIG. 1A. The first radiation source and the second radiation source are directed toward the tissue to deliver NIR radiation to the tissue. The first radiation source and the second radiation source can have a fixed distance from one another. Further, the first radiation source and the second radiation source can be positioned at a fixed distance to one or more detectors. Though described here as two radiation sources, a plurality of radiation sources may be used.

Once the radiation source is positioned, a first radiation can be delivered to the tissue, as in element 606. The first radiation can have a wavelength range of between about 650 nm and about 1000 nm. The tissue is at least partially transparent to the first radiation allowing the first radiation to travel a distance in the tissue. As the tissue is not homogenous, some components of the tissue, such as hemoglobin, will either absorb the first radiation, transmit the first radiation or reflect the first radiation based on the wavelength of the first radiation received. Radiation which is not absorbed is transmitted through the tissue creating a first transmitted radiation (also referred to as back-scattered radiation).

At least part of the first transmitted radiation is detected at a first detector, as in element 608. The first detector is positioned a first distance from the radiation source. The path that the radiation travels from the radiation source to the detector is the mean radiation path. The first distance determines the length of the mean radiation path from the radiation source to the detector as well as the depth of the detection. The hemoglobin, both HHb and $HbO_2$, within the mean radiation path will provide information in the form of absorption of the first radiation in the mean radiation path. The first transmitted radiation received at the detector can then be used in conjunction with other information to determine the contents of the mean radiation path.

The wavelength used, as described above, is important to the determination of the contents of the mean radiation path. The first detector detects the intensity of the first transmitted radiation of the wavelength produced by the radiation source. The intensity of the first transmitted radiation delivered to the detector will be affected by the overall amount of the first radiation within the mean radiation path and the amount of the first radiation which is absorbed by components which are spatially within the mean radiation path. The amount of the first radiation within the mean radiation path is a function of the absorption coefficient and the scattering coefficient of each layer of the tissue, which is empirically determined either prior to or during the measurement. The absorption is dependent on the wavelength used and the absorbing components in the tissue, which in this case are HHb and $HbO_2$. Both subtypes absorb radiation of wavelengths between about 650 nm and about 1000 nm to some degree. However, since 808 nm is the isosbestic point for HHb and $HbO_2$, the absorption by HHb is higher at wavelengths below 808 nm and $HbO_2$ is higher at wavelengths above 808 nm.

Once the first transmitted radiation is detected, a second radiation can be delivered from a second radiation source to the tissue, as in element 610. The second radiation source can have a wavelength between about 650 nm and about 1000 nm. The second radiation can be a single wavelength or a combination of wavelengths. Further, the second radiation can include one or more of the same wavelengths as the wavelengths of the first radiation. The tissue can absorb a portion of the second radiation creating a second transmitted radiation.

The second transmitted radiation is then detected at the detector positioned a second distance from the second radiation source, as in element 612. The path traveled by the second transmitted radiation through the tissue creates a second mean radiation path. The second distance may be the same as the first distance, such as when the first radiation source and the second radiation source are positioned in concentric circles which are at a specific radius from a centrally located detector.

The available radiation sources, such as the first radiation source and the second radiation source, are multiplexed, assuring that any one detector is only receiving radiation from one radiation source at any given time. As used herein, "multiplexed" refers to the delivery of the radiation from the source to the tissue and ultimately to each of the detectors, such that each of the detectors only receive radiation from one source at any given time. In one embodiment, multiplexing is done by timing the radiation delivery of each radiation source, such that no more than one radiation source is delivering radiation at any given time. Here, the first radiation is emitted from the first radiation source and a portion of the first radiation is received by the detector as the first transmitted radiation. Once the first transmitted radiation is received, the second radiation source emits the second radiation, a portion of which is received by the same detector. Thus when using time multiplexing, only one optical source is active at a time. Hence, the light detected by one or more photodetectors can be associated with the only radiation source active in that moment. Multiplexing the radiation sources both allows the control unit to differentiate between the sources of the radiation and allows for a larger number of mean radiation paths.

Though the multiplexing above is described with relation to time, the separation of optical signals emitted by distinct emitters (i.e., in distinct locations and/or distinct wavelengths) towards one (or more) photodetectors can be achieved with several techniques, such as time multiplexing (described above), frequency multiplexing, and code multiplexing.

With frequency multiplexing, the radiation sources are separated based on the frequency of the radiation produced by the radiation sources, such that the radiation sources can emit radiation simultaneously. To separate the signals received by the detector, the active radiation sources are modulated at a different frequency. In one example, three radiation sources, R1, R2 and R3, deliver radiation at 660 nm to a tissue. The wavelengths used herein are exemplary. Any wavelength or range of wavelengths for the determination of HbO2 and HHb as described h may be used. As described here, R1 produces the 660 nm radiation at a first frequency, F1; R2 produces the 660 nm radiation at a second frequency, F2; and R3 produces the 660 nm radiation at a third frequency, F3. As R1, R2 and R3 are delivering their radiation simultaneously, the radiation will be received at the detector as a single composite signal. The single composite signal yielded by the detector can then be demodulated at frequencies F1, F2 and F3 to reconstruct the three radiation signals which would have been obtained if the three radiation sources were emitted separately.

With code multiplexing, the radiation sources are separated based on information encoded into the radiation from the radiation sources, such that the radiation sources can emit radiation simultaneously. To separate the signals received by the detector, the active radiation sources are encoded with different codes. In one example, three radiation sources, R1, R2 and R3, deliver radiation at 880 nm to a tissue. As described here, R1 produces the 880 nm radiation with a first code, C1, embedded therein; R2 produces the 880 nm radiation with a second code, C2, embedded therein; and R3 produces the 880 nm radiation with a third code, C3, embedded therein. As R1, R2 and R3 are delivering their radiation simultaneously, the radiation will be received at the detector as a single composite signal. The single composite signal yielded by the detector can then be demodulated at frequencies F1, F2 and F3 to reconstruct the three radiation signals which would have been obtained if the three radiation sources were emitted separately. The single composite signal yielded by the photodetector can then be decoded using C1, C2 and C3 to reconstruct the three original signals which would have been obtained if the three sources were emitting in a time-multiplexed fashion.

Once the second transmitted radiation has been detected, an overlap absorbance between the first mean radiation path and the second mean radiation path can be determined, as in element 614. The first mean radiation path is calculated to have a specific three dimensional shape, based on the tissue, the interdistance between the radiation source and detector, scattering coefficient and other factors. The three dimensional shape of the mean radiation path is associated with the detected absorbance for each of the first transmitted radiation (the first mean radiation path) and the second transmitted radiation (the second mean radiation path). Assuming that there is overlap between the mean radiation path for the first transmitted radiation and the second transmitted radiation, the overlap absorbance is then determined. The overlap absorbance is a weighted absorbance of each of the first mean radiation path and the second mean radiation path based on the respective intensities and the size of the overlap. The first absorbance, the second absorbance and the overlap absorbance in coordinate space act as in conjunction to provide position and intensity of the oxygenation state of the hemoglobin in the tissue.

The steps of delivery of the first radiation, the detection of the first transmitted radiation, the delivery of the second radiation, the detection of the second transmitted radiation and the determining of the overlap absorbance are then repeated using a plurality of first radiation sources and a plurality of second radiation sources to create a plurality of overlap absorbances, as in element 616. A more complete view of the oxygenation can be derived by increasing the number of sources and detectors as well as widening the space over which the detection occurs. Overlapping mean radiation paths using wavelengths both above and below the isosbestic point, allow for positioning and separation of HHb and $HbO_2$.

Finally, the plurality of overlap absorbances is then mapped on a coordinate plane, as in element 618. The position of the overlap absorbance is known in comparison to the device. As such, the overlap absorbances are then plotted on an x, y and z axis with relation to the position of the device, where the position of the device is an arbitrary position in the coordinate plane. The position of the device can be mapped as well. The higher the number of overlapping mean radiation paths and the higher the number of overlapping areas of overlap at various wavelengths, the better the resolution of the image produced. Further, the longer the interdistance between the radiation sources and the detectors, the deeper the mean radiation path. The method above can be performed in a continuous fashion, such that the map of the tissue is updated in near real-time.

Figure 7:
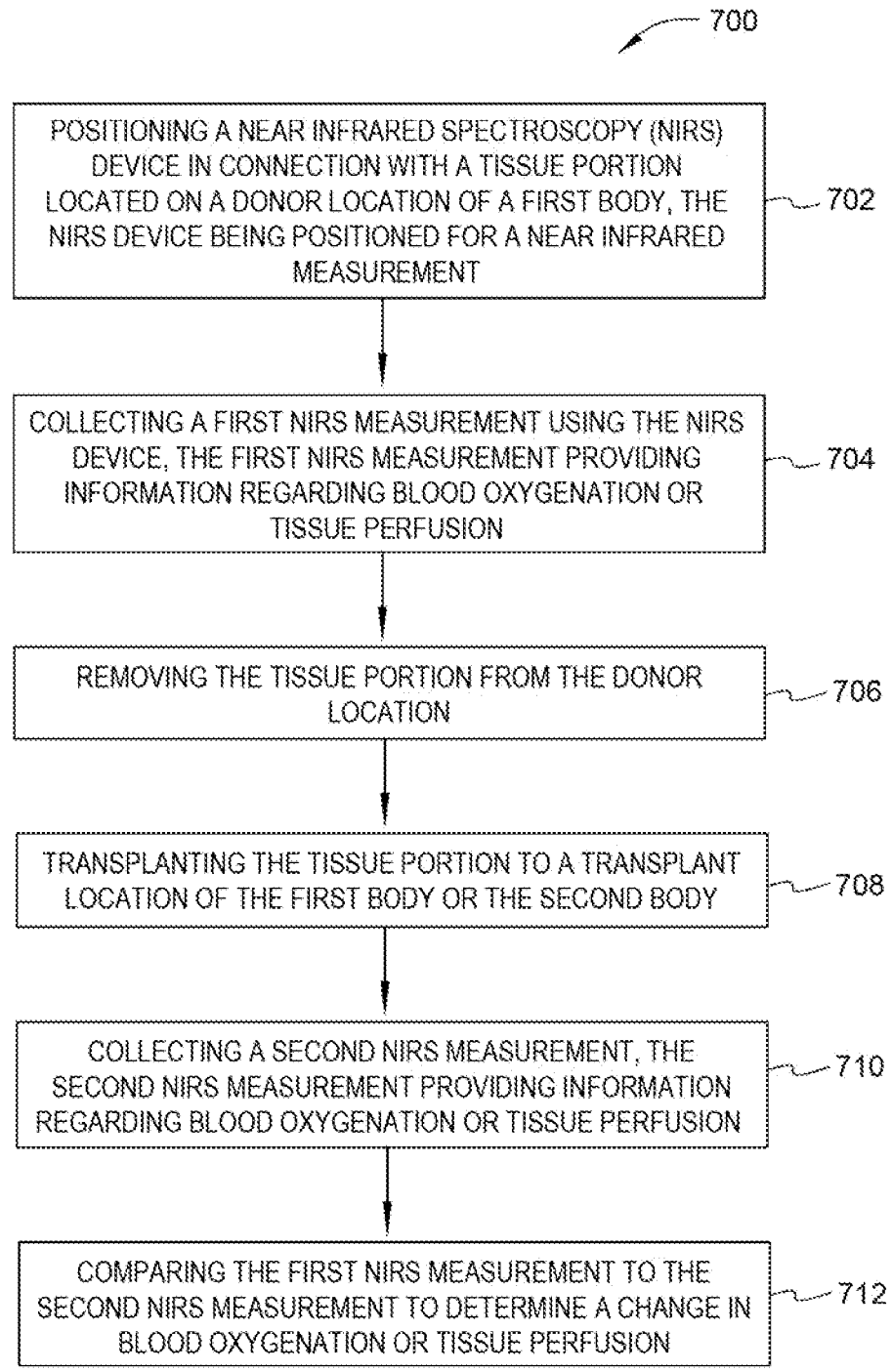
FIG. 7 is a block diagram of a method of transplanting a tissue, according to one embodiment.

FIG. 7 is a block diagram of a method 700 of transplanting a tissue, according to one embodiment. Tissue transplantation involves the relocation of a tissue from one site to another. By creating a pre-transfer and post-transfer volumetric map, possible blockages or anomalies can be detected early before tissue damage occurs. The method 700 can include positioning a near infrared spectroscopy (NIRS) device in connection with a tissue portion located on a donor location of a first body, the NIRS device being positioned for a near infrared measurement, at 702; collecting a first NIRS measurement using the NIRS device, the first NIRS measurement providing information regarding blood oxygenation or tissue perfusion, at 704; removing the tissue portion from the donor location of the first body, at 706; transplanting the tissue portion to a recipient location of the first body or a second body, at 708; collecting a second NIRS measurement, the second NIRS measurement providing information regarding blood oxygenation or tissue perfusion, at 710; and comparing the first NIRS measurement to the second NIRS measurement to determine a change in blood oxygenation or tissue perfusion, at 712. The method 700 can be performed sequentially as shown.

The method 700 begins by positioning a near infrared spectroscopy (NIRS) device in connection with a tissue portion located on a donor location of a first body, the NIRS device being positioned for a near infrared measurement, at 702. The NIRS device can be a NIRS device as described above in FIG. 1A-1D. Further, the NIRS device may include machine-readable instructions as described with relation to FIG. 2. The tissue portion can be positioned directly in contact with the NIRS device or intervening structures may be used. The tissue type may be a variety of tissue types including combinations of tissue types, such as epithelial tissue or adipose tissue.

With the NIRS device in position, a first NIRS measurement is collected using the NIRS device, the first NIRS measurement providing volumetric information regarding blood oxygenation or tissue perfusion, at 704. The first NIRS measurement can be a baseline measurement, which provides volumetric information as to tissue perfusion, comparative concentrations of HHb or $HbO_2$ or other oxygenation parameters. Future data can then be compared to the first NIRS measurement. Further, the first NIRS measurement may be a combination of any oxygenation parameters, including any oxygenation parameters listed or described herein. In another embodiment, the first NIRS measurement is compared to a baseline oxygenation parameter, such as to determine if the tissue is capable of being used in a transplant. The first NIRS measurement is a volumetric measurement of the tissue, providing three dimensional data regarding the oxygenation parameter or parameters.

After collecting the first NIRS measurement, the tissue portion can be removed from the donor location of the first body, at 706. The tissue portion can be removed from the donor site using techniques well known in the art for transplantation of a tissue. In one embodiment, the NIRS device is left in place during the transfer process. The tissue can be a single tissue type or composed of multiple types.

Though the NIRS device is described with reference to a tissue flap, this should not be read as limiting of possible uses. The NIRS device can be used in a variety of situation not related to transfer of a tissue flap. The NIRS device can be used to assess healthy tissue perfusion during exercise or at rest; other disease states such a peripheral vascular disease/diabetic vascular compromise/coronary artery disease and congestive heart failure; and for transplants of all types, to include skin flap tissue and organ transplantation (e.g., renal, heart, liver and possibly lung)—some of which could be done from outside the body, while other embodiments might involve just using it intraoperatively (e.g., when the heart is being rewarmed after bypass), or possibly left inside the body as a permanent monitoring device (an adjunct to an implantable pacemaker or defibrillator).

The tissue portion can then be transplanted to a recipient location of the first body or a second body, at 708. The recipient location can be located on either the donor or a separate recipient. The tissue is transplanted using techniques that are well known in the art.

A second NIRS measurement can then be collected, the second NIRS measurement providing volumetric information regarding blood oxygenation or tissue perfusion, at 710. The second NIRS measurement collected will at least include one of the oxygenation parameters determined in the first NIRS measurement. The oxygenation parameter will be related to a physiological event in the tissue. In one example, a lower oxygenation can be related to a vascular occlusion. Though described as separate events, the first NIRS measurement and the second NIRS measurement may be derived from the same event or measurement. In one embodiment, the first NIRS measurement and the second NIRS measurement are data sets selected from a continuous measurement.

The first NIRS measurement to the second NIRS measurement can be compared to determine a change in blood oxygenation or tissue perfusion, at 712. The first NIRS measurement is related to the tissue as perfused at the donor location and prior to disconnection from the native vasculature. The second NIRS measurement occurs after the reconnection of the tissue at the donor site. Thus, the comparison of the first NIRS measurement to the second NIRS measurement will show areas of deoxygenation, blood pooling occlusion or other issues which may need either pharmaceutical or surgical intervention.

Methods, systems and devices described herein disclose the use NIRS to provide more complete view of oxygenation in a tissue during reconstructive surgery or to track tissue perfusion in the setting of a limb crush injury that has resulted in compartment syndrome. By directing NIRS radiation of a specific wavelength toward a tissue in a multiplexed fashion, the absorbance of a known region and a known wavelength by the tissue can be determined. The detected absorbances are then plotted into a grid. These absorbances directly correlate with the location of HHb and HbO2, thus providing a map of blood flow to the tissue in a near-instantaneous fashion while avoiding user error.

While the foregoing is directed to embodiments of the inventions, other and further embodiments of the inventions may be devised without departing from the basic scope thereof.

The invention claimed is:

1. A method for tissue imaging in a transplanted tissue, sequentially comprising:
   positioning a near infrared spectroscopy (NIRS) device in connection with a tissue portion located on a donor location of a first body, the NIRS device being positioned for a near infrared measurement;
   collecting a first NIRS measurement using the NIRS device, the first NIRS measurement providing information to create a pre-transfer volumetric map regarding blood oxygenation or tissue perfusion;
   creating the pre-transfer volumetric map regarding blood oxygenation or tissue perfusion from the first NIRS measurement;
   removing the tissue portion from the donor location of the first body;
   transplanting the tissue portion to a recipient location of the first body or a second body;
   collecting a second NIRS measurement, the second NIRS measurement providing information to create a post-transfer volumetric map regarding blood oxygenation or tissue perfusion;
   creating the post-transfer volumetric map regarding bloody oxygenation or tissue perfusion from the second NIRS measurement; and
   comparing the pre-transfer volumetric map to the post-transfer volumetric map to determine a change in blood oxygenation or tissue perfusion.

2. The method of claim 1, wherein the NIRS device is connected with the tissue portion when the tissue portion is removed from the donor location and while the tissue portion is transplanted to the recipient location.

3. The method of claim 1, wherein the NIRS device comprises a plurality of first radiation sources, a plurality of second radiation sources and a plurality of detectors connected to a support.

4. The method of claim 3, wherein the first radiation sources and the second radiation sources are multiplexed.

5. The method of claim 4, wherein the first radiation sources each deliver a first radiation, and wherein the first radiation is a radiation with a wavelength between 650 nm and 800 nm.

6. The method of claim 4, wherein the second radiation sources each deliver a second radiation, wherein the second radiation is a radiation with a wavelength between 800 nm and 1000 nm.

7. The method of claim 4, wherein the first NIRS measurement and the second NIRS measurement are selected samples from a continuous NIRS measurement.

8. The method of claim 1 wherein:
   the pre-transfer volumetric map comprises dimensions corresponding to the tissue portion located on the donor location of the first body; and
   the post-transfer volumetric map comprises dimensions corresponding to the tissue portion located on the recipient location of the first body or the second body.

* * * * *